US007052455B2

United States Patent
Hale et al.

(10) Patent No.: US 7,052,455 B2
(45) Date of Patent: May 30, 2006

(54) INTERFACE FOR A VARIABLE DIRECTION-OF-VIEW ENDOSCOPE

(75) Inventors: Eric L. Hale, South Pasadena, CA (US); Nathan J. Schara, Pasadena, CA (US); Hans D. Hoeg, Arcadia, CA (US)

(73) Assignee: Karl Storz Development Corp., Goleta, CA (US)

( * ) Notice: Subject to any disclaimer, the term of this patent is extended or adjusted under 35 U.S.C. 154(b) by 346 days.

(21) Appl. No.: 10/734,688

(22) Filed: Dec. 12, 2003

(65) Prior Publication Data

US 2004/0127769 A1    Jul. 1, 2004

Related U.S. Application Data

(63) Continuation-in-part of application No. 10/020,374, filed on Dec. 14, 2001, now Pat. No. 6,663,559.

(51) Int. Cl.
*A61B 1/04* (2006.01)

(52) U.S. Cl. ...................................... 600/118; 600/173

(58) Field of Classification Search ................ 600/109, 600/117, 118; 606/130; 348/65, 74

See application file for complete search history.

(56) References Cited

U.S. PATENT DOCUMENTS

| 4,697,577 | A | * | 10/1987 | Forkner ...................... 600/173 |
| 5,313,306 | A | | 5/1994 | Kuban |
| 5,524,180 | A | | 6/1996 | Wang |
| 5,776,050 | A | * | 7/1998 | Chen et al. .................. 600/117 |
| 5,876,325 | A | * | 3/1999 | Mizuno et al. .............. 600/102 |
| 5,907,664 | A | | 5/1999 | Wang |
| 5,954,634 | A | | 9/1999 | Igarashi |
| 6,097,423 | A | | 8/2000 | Mattsson-Boze |
| 6,371,909 | B1 | * | 4/2002 | Hoeg et al. .................. 600/173 |
| 6,428,470 | B1 | * | 8/2002 | Thompson ................... 600/173 |
| 2002/0022767 | A1 | * | 2/2002 | Dohi et al. .................. 600/173 |

* cited by examiner

Primary Examiner—John P. Leubecker
(74) Attorney, Agent, or Firm—St. Onge Steward Johnston & Reens LLC

(57) ABSTRACT

An interface for a variable direction of view endoscope having an input device for receiving commands from the user, an output device for adjusting the endoscope, and an electronic processing device to determine the appropriate output based on the given input. The processing device may be configured to allow operation assisting features including a coordinate system aligned with the current view, a coordinate system aligned with the user's surroundings, a coordinate system aligned with the operating cavity, a memory to facilitate the immediate return to a user selected direction of view, and a clear indication of the current direction of view.

14 Claims, 8 Drawing Sheets

*Prior Art*

Prior Art

FIG. 3A

$$R_s(\theta_s, \phi_s, \zeta_s) = \begin{bmatrix} \cos\theta_s & -\sin\theta_s & 0 \\ \sin\theta_s & \cos\theta_s & 0 \\ 0 & 0 & 1 \end{bmatrix} \begin{bmatrix} \cos\phi_s & 0 & \sin\phi_s \\ 0 & 1 & 0 \\ -\sin\phi_s & 0 & \cos\phi_s \end{bmatrix} \begin{bmatrix} \cos\zeta_s & -\sin\zeta_s & 0 \\ \sin\zeta_s & \cos\zeta_s & 0 \\ 0 & 0 & 1 \end{bmatrix}$$

FIG. 3B

$$R_c(\theta_c, \phi_c, \zeta_c) = \begin{bmatrix} \cos\theta_c & -\sin\theta_c & 0 \\ \sin\theta_c & \cos\theta_c & 0 \\ 0 & 0 & 1 \end{bmatrix} \begin{bmatrix} \cos\phi_c & 0 & \sin\phi_c \\ 0 & 1 & 0 \\ -\sin\phi_c & 0 & \cos\phi_c \end{bmatrix} \begin{bmatrix} \cos\zeta_c & -\sin\zeta_c & 0 \\ \sin\zeta_c & \cos\zeta_c & 0 \\ 0 & 0 & 1 \end{bmatrix}$$

FIG. 3C

$$W = \begin{bmatrix} 0 & -Z & Y \\ Z & 0 & -X \\ -Y & X & 0 \end{bmatrix}$$

FIG. 3E $$\cos\theta_C(Y\cos\zeta_C + X\sin\zeta_C) + \sin\theta_C(Z\sin\phi_C + \cos\phi_C(X\cos\zeta_C - Y\sin\zeta_C)) = \dot{\zeta}_S\sin\theta_S\sin\phi_S + \dot{\phi}_S\cos\theta_S$$

FIG. 3F $$-\sin\theta_C(Y\cos\zeta_C + X\sin\zeta_C) + \cos\theta_C(Z\sin\phi_C + \cos\phi_C(X\cos\zeta_C - Y\sin\zeta_C)) = \dot{\zeta}_S\cos\theta_S\sin\phi_S - \dot{\phi}_S\sin\theta_S$$

FIG. 3G $$Z\cos\phi_C + \sin\phi_C(-X\cos\zeta_C + Y\sin\zeta_C) = \dot{\zeta}_S\cos\phi_S + \dot{\theta}_S$$

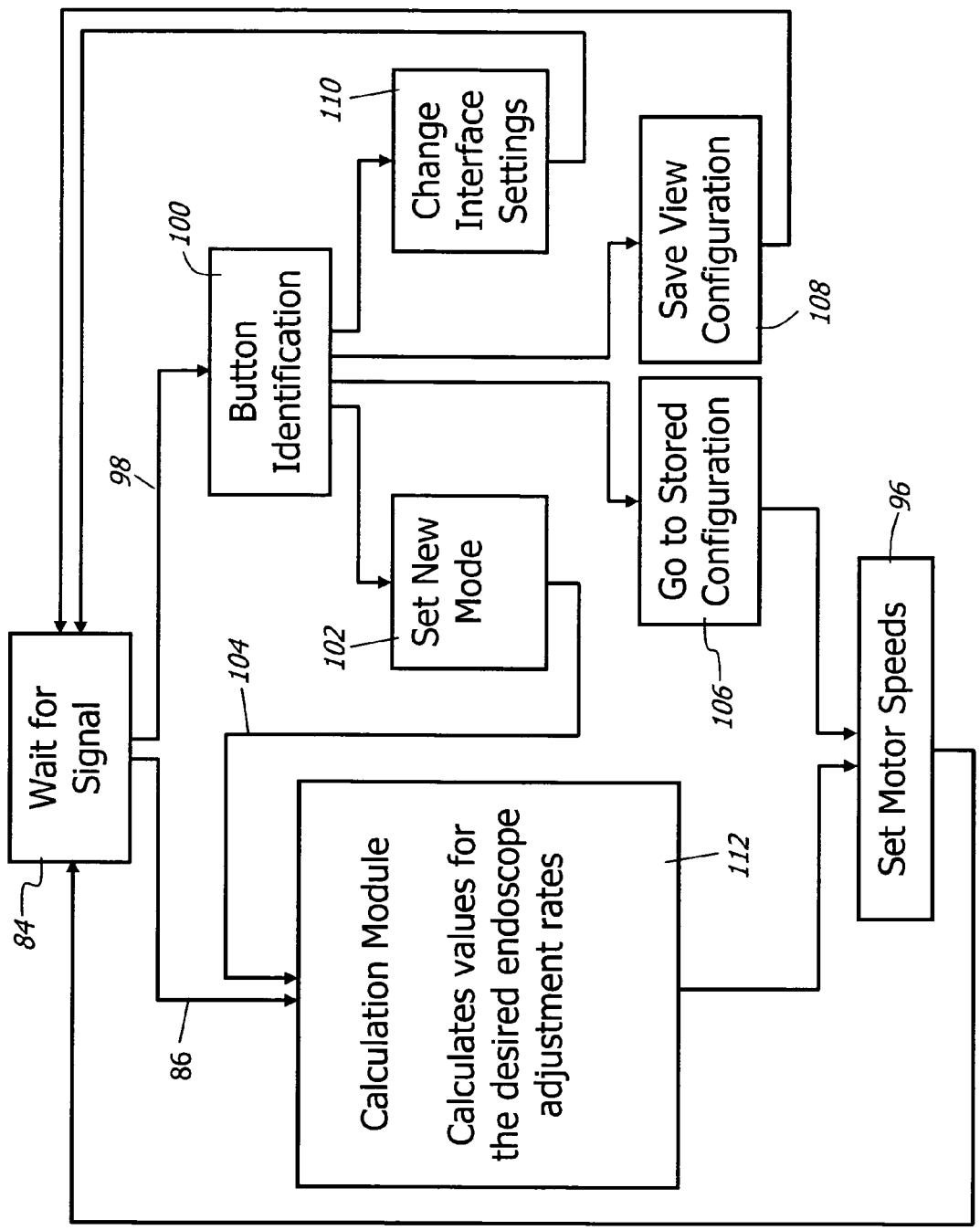

INTERFACE FOR A VARIABLE DIRECTION-OF-VIEW ENDOSCOPE

CROSS-REFERENCE TO PRIOR APPLICATIONS

This application is a continuation-in-part of application Ser. No. 10/020,374, filed Dec. 14, 2001, now U.S. Pat. No. 6,663,559.

STATEMENT REGARDING FEDERALLY SPONSORED RESEARCH OR DEVELOPMENT

Not Applicable.

REFERENCE TO A COMPACT DISK APPENDIX

Not Applicable.

BACKGROUND OF THE INVENTION

The present invention relates to endoscopes (including devices such as borescopes, fiberscopes, etc.) and specifically to control of endoscopes capable of varying their direction of view.

Endoscopes are elongated devices used to visualize the insides of cavities. Recent developments have brought about endoscopes capable of varying their direction of view. The purpose of these endoscopes is to allow the user to scan over a larger area with less device movement than traditional endoscopes and provide greater flexibility in obtaining a desired view.

Most endoscopes capable of varying their direction of view include mechanically steered optical components. These are controlled using one or more knobs or similar devices for adjusting the degrees of freedom available in the endoscope along the respective axis of each degree. Examples of these are disclosed in U.S. Pat. No. 3,880,148 to Kanehira et al. (1975), U.S. Pat. No. 4,697,577 to Forkner (1987), U.S. Pat. No. 3,572,325 to Bazell et al. (1971), and U.S. Pat. No. 6,371,909 to Høeg et al. (2002), each of which is incorporated herein by reference in its entirety. In all of these examples, each axis of adjustment is controlled independently. Making a desired compound adjustment involving two or more axes is difficult to accomplish, requiring multiple hands and/or great dexterity.

Other endoscopes capable of varying their direction of view include those disclosed in U.S. Pat. No. 5,954,634 to Igarashi (1998) and U.S. Pat. No. 5,313,306 to Kuban, et al. (1994), each of which is incorporated herein by reference in its entirety. These devices provide a viewed area variably selected from within a wide-angle captured image giving a result similar to those with mechanically adjusted optical components. Like mechanically adjusted variable direction of view endoscopes, these devices may only be adjusted in a predetermined manner with predetermined axes.

Each of the above endoscopes has a set of adjustment axes that define a natural coordinate system for that endoscope. In the natural coordinate system, each degree of freedom of the endoscope is one axis of the coordinate system. Each endoscope is controlled in relation to its natural coordinate system. Due to differences in the design of varying endoscopes, each endoscope's natural coordinate system may be different. This can create a significant problem for users when attempting to work with a different endoscope than that to which they are accustomed. The natural coordinate system of an endoscope is always aligned with that endoscope rather than with the user's surroundings or the operating cavity. The user can become confused and disoriented when trying to selectively scan within a coordinate system that fails to align with a familiar environment.

Because the distal end of a variable direction of view endoscope is generally not visible during use, the user often requires an external indication of the current viewing direction. Some endoscopes fail to have any method of indicating the direction of view, while others include indicators that are inconvenient or difficult for the user to interpret. Not knowing the current direction of view makes it challenging to adjust to a desired direction of view or find a particular feature within the cavity. Additionally, returning to a previous direction of view can be quite challenging.

Although prior art variable direction of view endoscopes may have been designed for easy and efficient use, the interfaces heretofore known suffer from at least the following disadvantages: a) the interface provided with each endoscope can be unintuitive and confusing for the user; b) the disjoint control of multiple degrees of freedom makes precision compound adjustments prohibitively difficult to execute; c) various types of variable direction of view endoscopes require very different methods of operation; d) the control coordinate system available can not usually be aligned with the user's surroundings; e) the control coordinate system available can not usually be aligned with the operating cavity; f) the current direction of view can be difficult to determine; and g) the user must manually adjust the endoscope to return to a particular direction of view.

Some endoscopic control systems include actuators such as motors to assist the user in controlling the view. For example, U.S. Pat. No. 5,524,180 to Wang et al. (1996), which is incorporated herein by reference in its entirety, discloses a motorized control system for automated positioning of an endoscope. Such control systems utilize a computer and robotic arm to control the movement of an endoscope for the purpose of changing the viewing direction. However, instead of moving the entire endoscope, variable direction of view endoscopes should be controlled in a way that utilizes their internal direction of view adjustment systems. Therefore, existing electro-mechanical endoscope control systems are not well suited to situations in which the use of a variable direction of view endoscope is desired.

Accordingly, the primary object of the present invention is to provide an easy-to-use interface for a variable direction of view endoscope capable of adjusting multiple degrees of freedom of the endoscope simultaneously to execute precision compound adjustments. Another object of the present invention is to use this interface to mask the specific implementation of the endoscope from the user through a standard set of displays and controls. Yet another object of the present invention is to provide an interface having several different control coordinate systems for the user to choose between, enabling more efficient and effective procedures.

Various other objectives and advantages of the present invention will become apparent to those skilled in the art as more detailed description is set forth below.

BRIEF SUMMARY OF THE INVENTION

In accordance with the present invention, an interface for a variable direction of view endoscope comprises an input means for receiving commands from the user, an output means for adjusting the endoscope, and an electronic processing device to determine the appropriate output based on the given input. In certain embodiments, the processing device may be configured to allow operation-assisting features, including a control coordinate system aligned with the endoscope, a control coordinate system aligned with the current view, a control coordinate system aligned with the user's surroundings, a control coordinate system aligned with the operating cavity, a clear display of one or more coordinate systems, a memory to facilitate the immediate return to a user selected direction of view, and a clear indication of the current direction of view. As used herein, the following terms have the following meanings:

"Endoscope" refers to an endoscope (used for medical procedures) or any similar device such as a borescope, a fiberscope, etc.

"Endoscope configuration" refers to a set comprised of an orientation (or state) of each axis (or degree of freedom) of an endoscope.

"Control coordinate system" refers to the coordinate system with respect to which control inputs are made and interpreted.

"Natural coordinate system of an endoscope" refers to a coordinate system defined by the adjustment axes of an endoscope and may be used to parameterize a viewing direction and orientation with respect to the normal operation of that endoscope.

"Current view coordinate system" refers to a coordinate system which is always aligned with the current viewing direction and orientation.

An "arbitrary coordinate system" may be any other coordinate system related to the endoscope or its surroundings.

In one embodiment of the present invention, a system for viewing the inside of a cavity using a variable direction of view endoscope, wherein a view vector is located at a distal end of said endoscope comprises an input device that receives commands from a user, a tracking device that provides view vector orientation information, a processing device that receives said commands and said orientation information and performs operations comprising the calculation of desired endoscope adjustment rates based on said commands and said orientation information, wherein said commands are interpreted by said processing device with respect to a control coordinate system that can change in alignment with said endoscope, a control device that adjusts said endoscope according to said adjustment rates; and a display device that displays a current endoscopic view.

In another embodiment of the present invention, a system for viewing the inside of a cavity using a variable direction of view endoscope, wherein a view vector is located at a distal end of said endoscope comprises an input device that receives commands from a user, a tracking device that provides view vector orientation information, a processing device that receives said commands and said orientation information and performs operations comprising the calculation of a desired endoscope adjustment rates based on said commands and said orientation information, wherein said commands are interpreted by said processing device with respect to a control coordinate system that can change in alignment with said endoscope, and wherein said endoscope adjusts at said adjustment rates, and a viewing device that provides a current endoscopic view.

In another embodiment of the present invention, a system for viewing the inside of a cavity using a variable direction of view endoscope, wherein a view vector is located at a distal end of said endoscope comprises an input means for receiving commands from a user, a tracking means for providing view vector orientation information, a processing means for receiving said commands and said orientation information and for performing operations, comprising the calculation of desired endoscope adjustment rates based on said commands and said orientation information, wherein said commands are interpreted by said processing device with respect to a control coordinate system that can change in alignment with said endoscope, an adjusting means for adjusting said endoscope according to said adjustment rates, and a viewing means for providing a current endoscopic view.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 3A through 3G show the mathematical elements and formulas used to calculate appropriate adjustment rates.

FIG. 6 is a flow chart illustrating the operation of the central control unit according to the present invention.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1A:
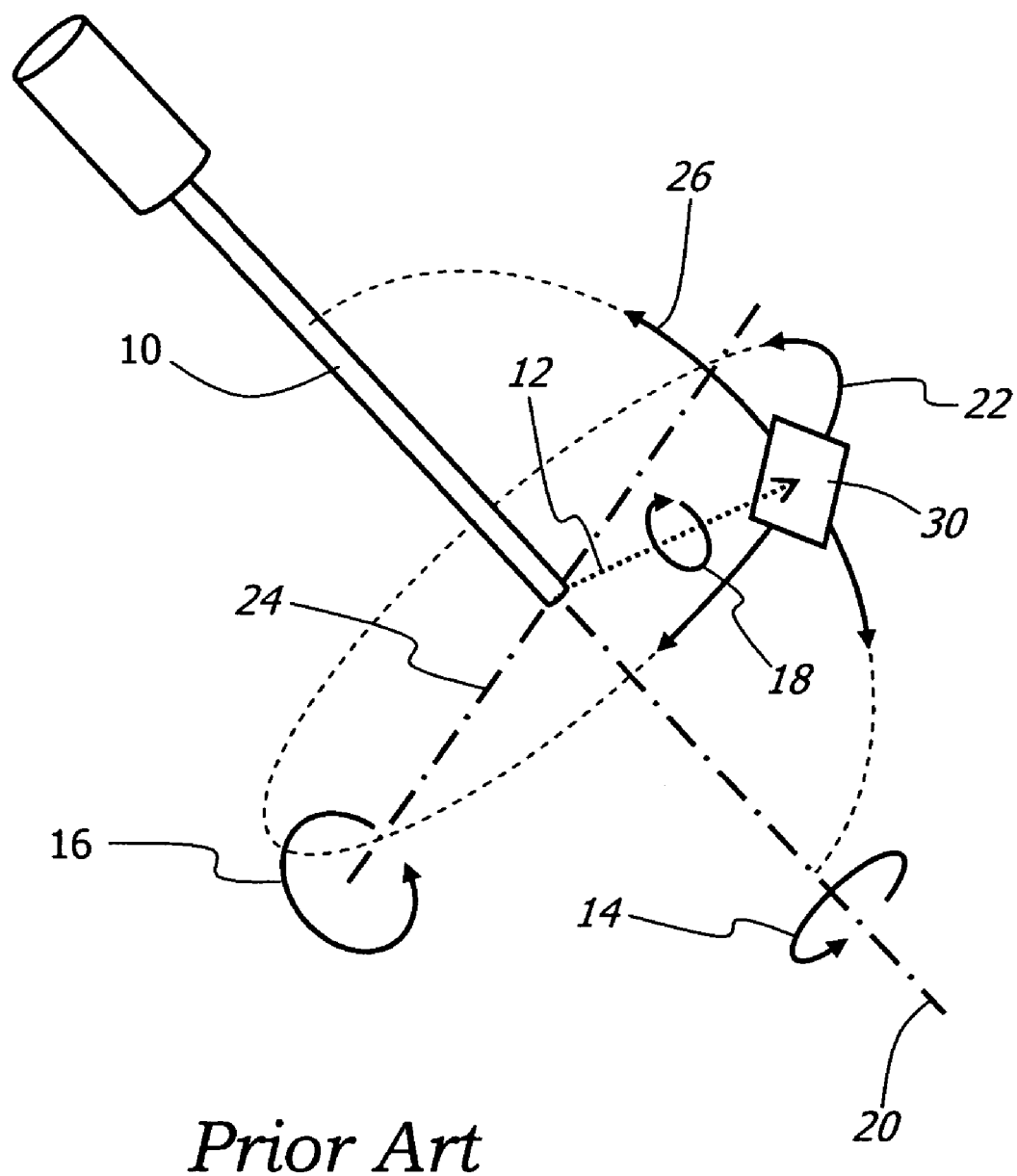
FIG. 1A, 1B, and 1C diagram the basic operational characteristics of the prior art.
Figure 1B:
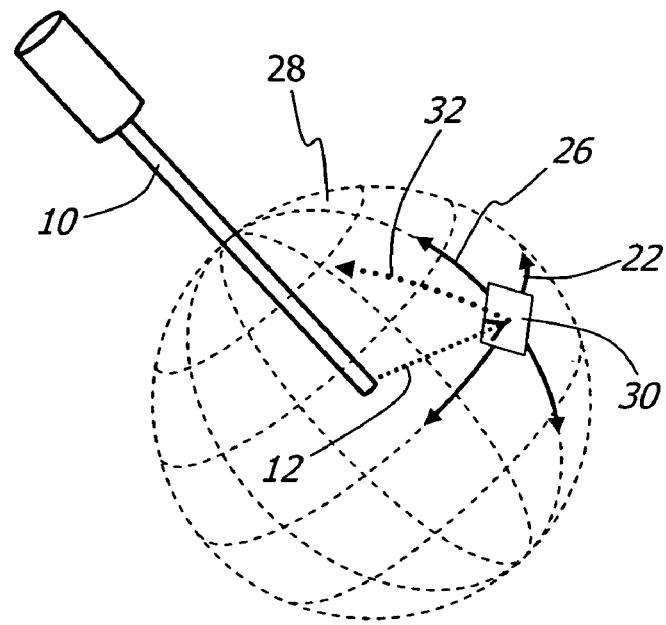

FIG. 1A is a diagram of a basic variable direction of view endoscope 10. Such an endoscope typically has a view vector 12 with at least two degrees of freedom 14, 16. The first degree of freedom 14 permits rotation of the view vector 12 about the longitudinal axis of the endoscope 20, which allows the view vector 12 to scan in a latitudinal direction 22. The second degree of freedom 16 permits rotation of the view vector 12 about an axis 24 perpendicular to the longitudinal axis 20, which allows the view vector 12 to scan in a longitudinal direction 26. These degrees of freedom define a natural endoscope coordinate system 28 as shown in FIG. 1B.

A third degree of freedom 18 may also be available because it is usually possible to adjust the rotational orientation of the endoscopic view 30. This is frequently accomplished by simply rotating an imaging device, such a camera, which is coupled to the proximal end of the endoscope. View rotation may also be provided using a prism built into the endoscope or by digitally rotating the image before viewing. Regardless of the method used, the view vector 12 is considered the axis of rotation for the view 30.

Figure 1C:
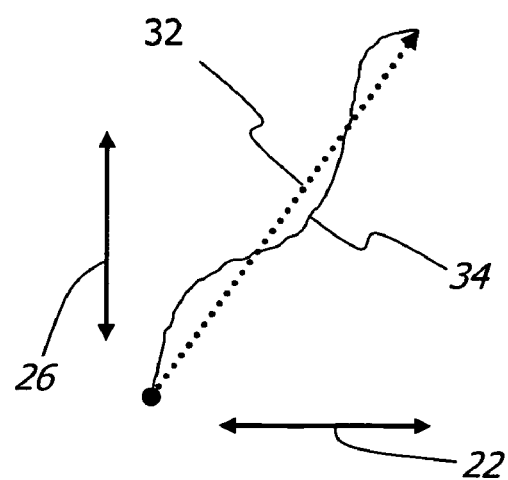

A user typically controls the view by adjusting the first degree of freedom 14 and second degree of freedom 16 to select a desired direction for the view vector 12. The axes may be adjusted separately or at the same time. Once the desired direction has been obtained, the rotational orientation of the resulting image is adjusted as desired. However, because each adjustment axis is controlled independently, scanning along an arbitrary path 32 that does not line up with either of the principal scanning directions 22, 26 is not easily accomplished. This discrepancy is demonstrated in FIG. 1C which depicts a typical path 34 traced by the view vector 12 of a traditional variable direction of view endoscope 10 while attempting to achieve the desired scan path 32. The foregoing scenario can readily be likened to the challenging problem of trying to appropriately adjust the two knobs of an Etch-A-Sketch®, described in U.S. Pat. No. 3,760,505 to Clark, in order to draw a desired diagonal line or curve. Moreover, when the rotational orientation of the view is adjusted, changing the apparent directions of the axes, this problem is worsened.

Figure 2:
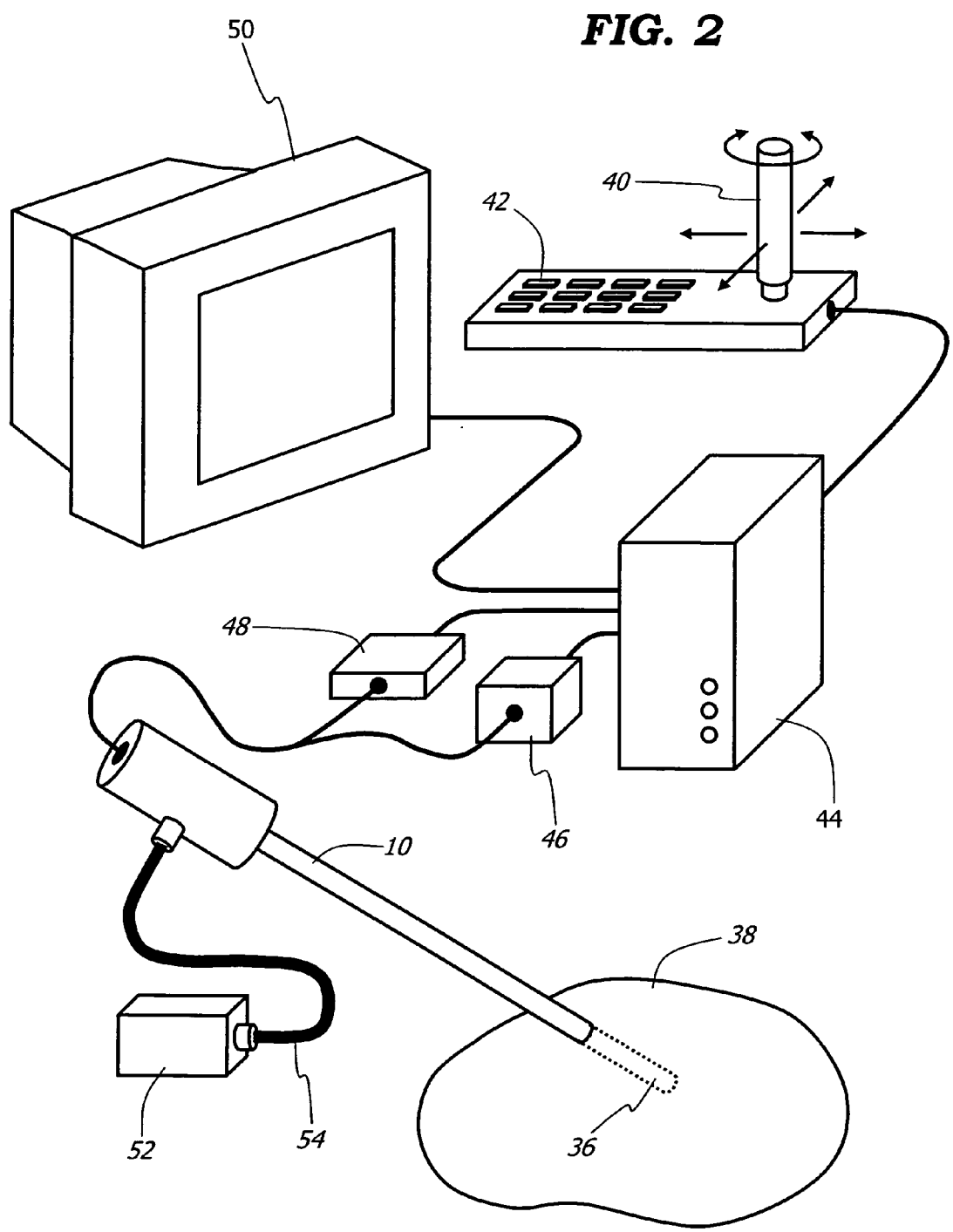
FIG. 2 is an illustration of a complete endoscopic operating system according to the present invention.

A preferred embodiment of a complete endoscopic viewing system, including the interface system of the present invention, is described herein with reference to FIG. 2. A variable direction of view endoscope 10, similar to the one shown in FIG. 1A, is positioned with its distal end portion 36 in a cavity to be examined 38. The endoscope is equipped with small motors (not shown) that enable electronic control of each degree of freedom of the endoscope, and encoders (not shown) that provide information about of the current orientation of the view about each respective axis. The motors and encoders permit each axis to be parameterized as a variable with a value ranging from −180 degrees to +180 degrees. In this way, the view vector may be controlled and tracked. A three-axis joystick 40 gives a user left/right, up/down, and counter-clockwise/clockwise input capabilities. These inputs can be parameterized as +/−X, +/−Y, and +/−Z, respectively. The joystick is used to select desired viewing adjustments. In some embodiments, the joystick 40 is attached to the endoscope 10. A keypad 42 facilitates additional input such as mode and display settings. Alternatively, these inputs could be selected from a menu using the joystick 40.

The inputs are received by a central control unit 44. The central control unit 44, a computer in the preferred embodiment, processes input from the user and information from the endoscope encoders to establish an appropriate adjustment rate for each axis. The appropriate adjustment rates are based on a control coordinate system and may be dependent upon previous inputs, adjustments, and endoscope configurations. Once the appropriate adjustment rates have been calculated, the adjustment information is provided to a motor control unit 46. The motor control unit 46 controls the endoscope configuration through the motors in the endoscope 10. Specifically, the motor control unit 46 sets the rates of the motors. Upon the completion of the rate adjustment, the interface system is ready for another input. The process will repeat to maintain the appropriate adjustment rates. An image acquisition unit 48 receives image signals from the endoscope 10 and adjusts the signals as needed. The central control unit 44 receives the adjusted signals from the image acquisition unit 48. An endoscopic video image and additional relevant information are relayed to a video display device 50 for presentation to the user. Illumination for the cavity 38 is delivered through the endoscope 10 from a standard light source 52 via a standard light guide 54. In alternative embodiments of the invention, the various components of the endoscopic viewing system are combined such that each module performs multiple functions.

The following variables are provided in the interface system for storing the encoder values corresponding to the current endoscope configuration relative to the default configuration of the endoscope:

$\theta_s$=the angle of the view vector about the longitudinal axis of the endoscope (first degree of freedom).

$\phi_s$=the angle of the view vector about the axis perpendicular to the longitudinal axis (second degree of freedom).

$\zeta_s$=the angle of the arbitrary rotational orientation of the view (third degree of freedom).

The following variables are provided in the interface system for storing the orientation of a control coordinate system relative to the default configuration of the endoscope:

$\theta_c$=stores the encoder value describing the angle of the view vector about the longitudinal axis of the endoscope when the view is aligned at a pole of the control coordinate system.

$\phi_c$=stores the encoder value describing the angle of the view vector about the axis perpendicular to the longitudinal axis when the view is aligned at the pole of the control coordinate system.

$\zeta_c$=stores the encoder value describing the angle of the arbitrary rotational orientation of the view when the view is aligned at the pole of the control coordinate system.

The following variables are provided in the interface system for storing the appropriate adjustment rate for each axis:

$\dot{\theta}_s$=the angular velocity of the view vector about the longitudinal axis of the endoscope (first degree of freedom).

$\dot{\phi}_s$=the angular velocity of the view vector about the axis perpendicular to the longitudinal axis (second degree of freedom).

$\dot{\zeta}_s$=the angular velocity of the arbitrary rotational orientation of the view (third degree of freedom).

The following variables are provided in the interface system for storing the inputs from the joystick:

X=the input value of the joystick Y axis displacement (X axis rotation).

Y=the input value of the joystick X axis displacement (Y axis rotation).

Z=the input value of the joystick Z axis rotation.

Matrices are used to calculate the desired endoscope adjustment rates. The rotation matrix of FIG. 3A describes the orientation of the current view relative to the default position of the endoscope. The rotation matrix of FIG. 3B describes the orientation of a current control coordinate system 70 relative to the default position of the endoscope. The matrix of FIG. 3C describes the input angular velocity specification. The above matrices are related by the equation of FIG. 3D. The equation of FIG. 3D leads to the equations of FIGS. 3E, 3F, and 3G. These equations are used to solve for the appropriate adjustment rate for each axis.

In the preferred embodiment, various modes of operation are provided for the user. A first mode of operation can be thought of as an endoscope-frame mode. In this mode, the control coordinate system is aligned with the natural coordinate system of the endoscope. Inputs from the user are effectively applied directly to the endoscope motors. Each axis of the joystick is effectively a speed control for an axis of the endoscope. Endoscope-frame mode is very similar to the standard operation of a variable direction of view endoscope. Although operation of the endoscope is still limited to the natural coordinate system of the endoscope, easily specified compound adjustments can be precisely carried out by the interface system. However, in this mode it may still be difficult for a user to determine his or her desired adjustment as the orientation of each axis of motion is not constant relative to the endoscopic view.

A second mode of operation, which can be thought of as view-frame mode, addresses this issue. The view-frame mode control coordinate system is always aligned with the current view. The user specifies desired adjustments based on the way in which the current view appears on the screen. Through control of the joystick, the user may choose a direction and speed to move the center of the view and a rotation for the rotational view orientation. For example, if the user wants to see to the left of the current view, he simply presses left. The interface then determines the best way to adjust the endoscope to achieve the desired adjustments. View-frame mode is ideal for making small adjustments to the current view.

In certain cases it may be preferable to operate while constrained to a coordinate system having fixed longitude and latitude. This is often the case when significant view adjustments are required and the user desires to maintain a greater sense of the relative locations of features within the viewed cavity. Unfortunately, the natural endoscope coordinate system will not usually be aligned with the viewed cavity in a convenient manner. Therefore, a third mode of operation, which can be thought of as free-frame mode, is provided.

Figure 4:
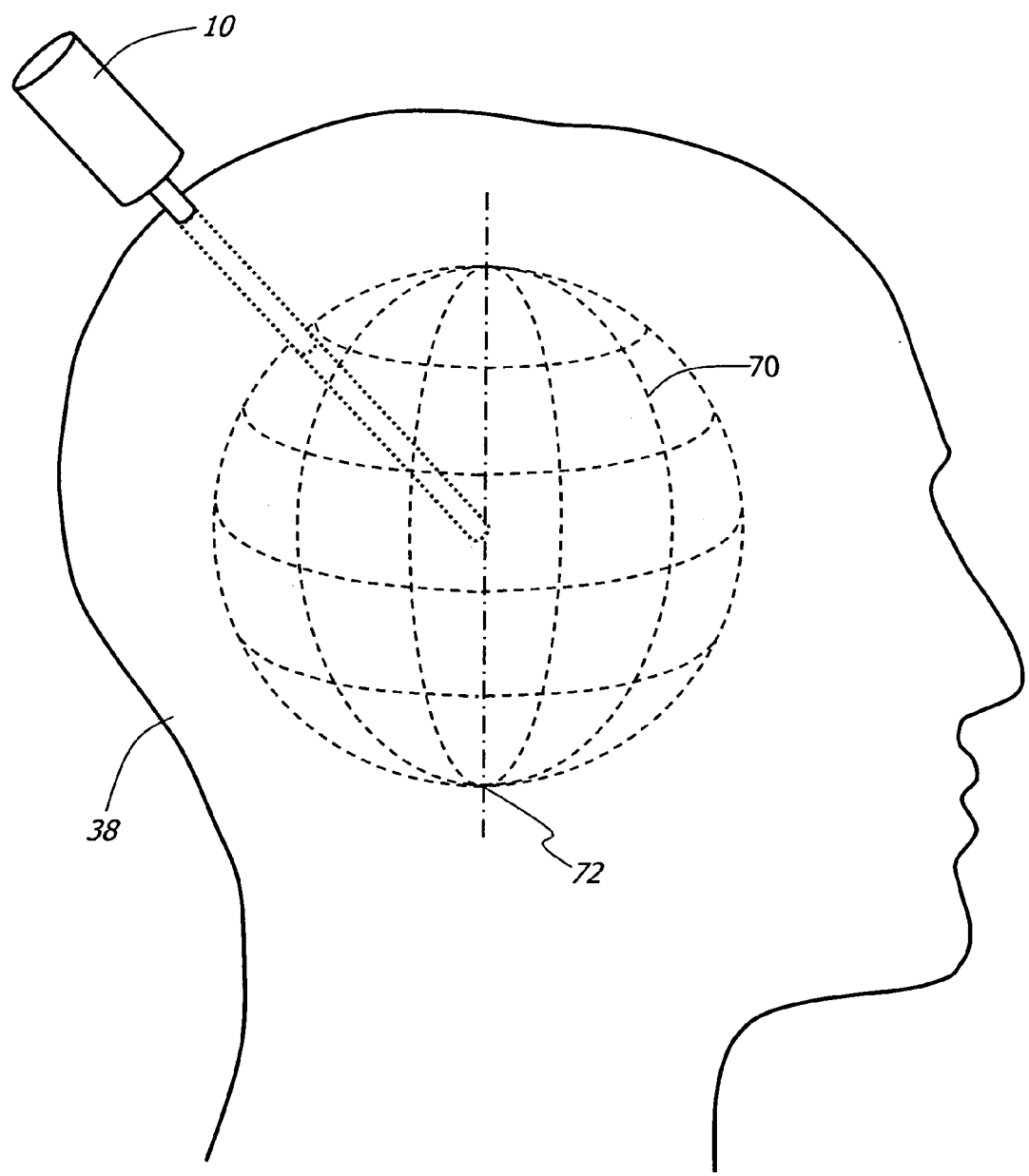
FIG. 4 is an illustration of an arbitrary coordinate system as defined by the free-frame mode of operation according to the present invention.

As shown in FIG. 4, the control coordinate system for specifying adjustments is aligned with an arbitrary coordinate system 70 defined within a cavity 38. The arbitrary coordinate system 70 may be aligned with gravity or with a particularly notable feature, and may be created automatically or based on a user's instructions. For example, the user may specify an orientation for an arbitrary coordinate system by selecting a direction to correspond with a pole of that arbitrary coordinate system. Alternatively, a coordinate system could be defined automatically based on the output of one or more gyroscopes or accelerometers responsive to gravity.

Inputs from the user are applied to adjust the view within the arbitrary coordinate system. The X value from the joystick is used to adjust longitude. The Y value from the joystick is used to adjust latitude. The Z value from the joystick may be used to adjust the view rotation. However, view rotation is usually held constant in free-frame mode to simplify the use of the arbitrary coordinate system.

Additional memory in the interface system enables the user to store multiple arbitrary coordinate systems. These coordinate systems may be configured independently, each based on a different set of preferences.

An alternative method of determining the appropriate adjustment rates is based on average angular velocity. First, a temporary desired endpoint is determined based on an input velocity in the control coordinate system and a time period. Ideally, the time period should approximate the period from one calculation cycle to the next. Longer time periods may be used when specifying greater adjustments. Based on the temporary desired endpoint, an appropriate adjustment magnitude is determined for each axis of the endoscope. These magnitudes are then divided by the time period to give the appropriate adjustment rates.

Memory is provided in the interface system for storing multiple sets of encoder variables. Each of the sets of encoder variables is a stored endoscope configuration. Each of the stored endoscope configurations corresponds to a view. The stored endoscope configurations enable the user to return to a previous view. To do this, the required adjustments from the present configuration to the stored goal are calculated and used to emulate normal joystick inputs.

Figure 5:
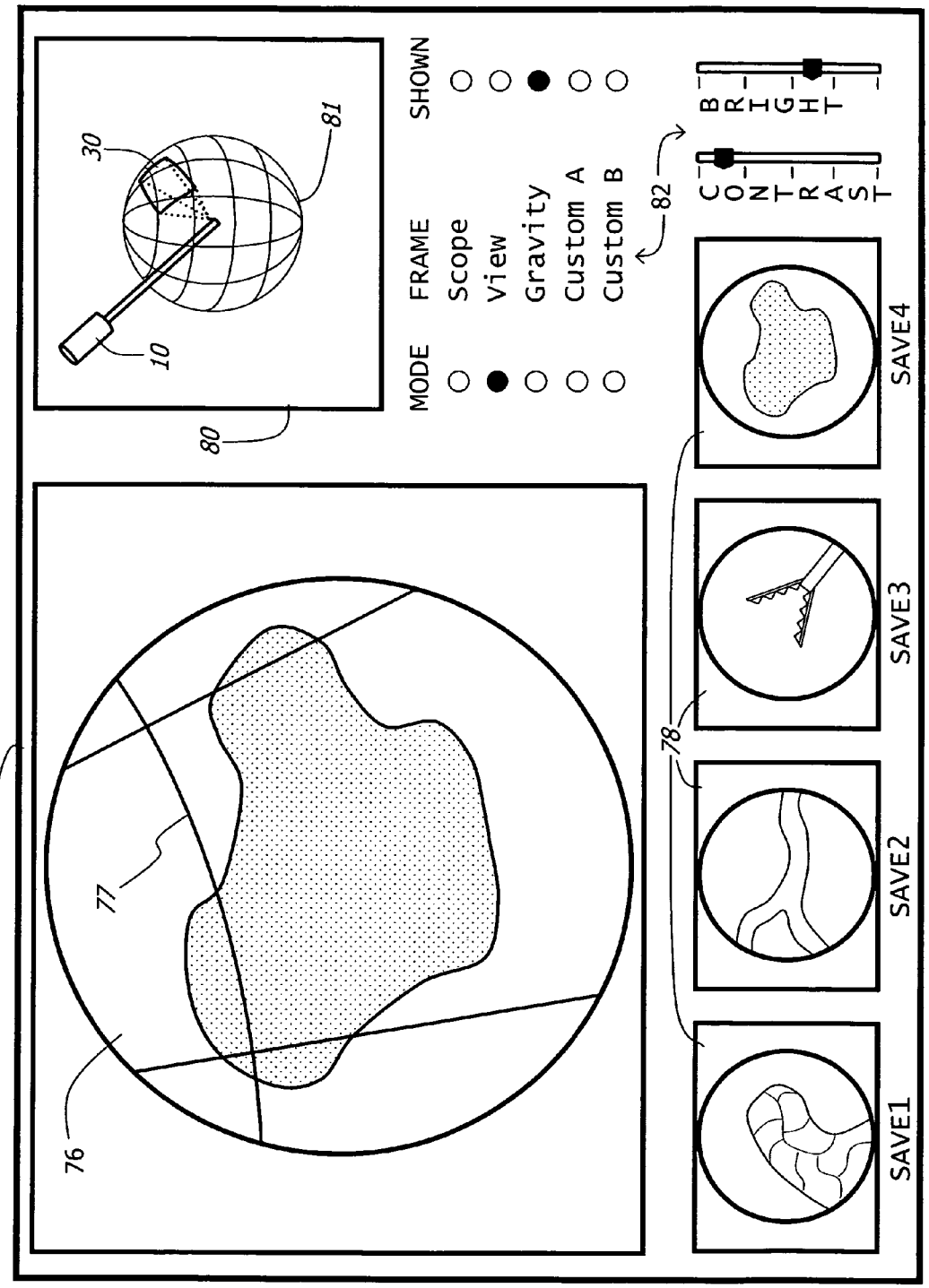
FIG. 5 shows a displayed output from the endoscopic operating system according to the present invention.

The endoscopic video image and additional relevant information are presented to the user in a convenient fashion on a video display device. FIG. 5 illustrates an embodiment of this presentation. The screen of the display device 74 is organized into multiple sections, each with a different purpose. A large section of the screen 74 is used to display a video image 76 from the endoscope. A representation of a coordinate system 77 may be graphically superimposed on the video image 76 to aid the user in understanding and using that coordinate system. Several smaller captured images 78 are provided, each one corresponding to a stored endoscope configuration. The captured images 78 act in place of names to allow a user to easily identify each stored endoscope configuration.

A computer generated depiction of the endoscope 80 is provided to assist the user in understanding the current view 30. The depiction 80 shows the endoscope 10 and the current view 30 from a viewpoint outside of the cavity. One or more coordinate systems 81 may also be shown in this depiction 80. Additionally, the depiction 80 may include simulated important features or other markings (not shown) to aid the situational understanding of the user. For example, a tumor to be removed, as located in a preoperative scan, could be shown in the depiction 80 to aid a surgeon in locating and identifying the tumor visually. In yet another section of the screen 74, the current mode and display settings 82 are displayed. In an alternative embodiment, the information discussed above may be displayed on multiple display devices. For example, the endoscopic image might be displayed separately from the other endoscopic operating system information.

FIG. 6 is a flow chart illustrating the operation of the central control unit 44, shown in FIG. 2, according to an embodiment of the invention. The central control unit 44 waits for a signal indicating user input 84. If it receives a joystick input 86, it prepares to perform the view adjustment desired by the user. The control unit calculates values for the desired endoscope adjustment rates 112 as described above. These values are then sent to the motor controller unit 46, which appropriately operates the motors 96. Once this command has been completed, the interface system waits for another input 84.

If the central control unit 44 receives a button input 98, it first identifies the type of button pressed 100. If the user has chosen to set a new mode 102, the mode is changed and the adjustment sequence is started 104. If the user has selected a stored endoscope configuration 106, the interface system instructs the endoscope to adjust directly to that endoscope configuration 96. If the user has elected to save the current endoscope configuration 108, the current endoscope configuration variables and current image are stored in memory before the interface system waits for another input 84. If the user has chosen to adjust the interface settings 110, the appropriate adjustment is made, and the interface system waits for another input 84.

Accordingly, the present invention provides an interface for a variable direction of view endoscope that is easy to use and capable of adjusting multiple degrees of freedom of the endoscope simultaneously and precisely according to the desires of the user.

The present invention has been described above in terms of a presently preferred embodiment so that an understanding of the present invention can be conveyed. However, there are many alternative arrangements for an interface for a variable direction of view endoscope and methods of operation not specifically described herein but with which the present invention is applicable. For example, the display features of the preferred embodiment of the present invention could be used in a system that does not control the endoscope. Although specific formulas were given for an endoscope of the type shown in FIG. 1, the interface of the present invention is useful with any type of variable direction of view endoscope when provided with calculation functions consistent with the operation of the endoscope selected. Some endoscope variations utilize electronic processing and memory instead of motors and encoders to accomplish view adjustments.

In addition, while the examples were given with respect to endoscopes for use in surgical procedures, the present invention is equally applicable with respect to borescopes or the like for use within various mechanical structures. The scope of the present invention should therefore not be limited by the embodiments illustrated, but rather it should be understood that the present invention has wide applicability with respect to multi-directional viewing instruments and procedures generally. All modifications, variations, or equivalent elements and implementations that are within the scope of the appended claims should therefore be considered within the scope of the invention.

We claim:

1. A system for viewing the inside of a cavity using a variable direction of view endoscope, wherein a view vector is located at a distal end of said endoscope, comprising:
   an input device that receives commands from a user;
   a tracking device that provides view vector orientation information;
   a processing device that receives said commands and said orientation information and performs operations comprising the calculation of desired endoscope adjustment rates based on said commands and said orientation information, wherein said commands are interpreted by said processing device with respect to a control coordinate system that can change in alignment with said endoscope;
   a control device that adjusts said endoscope according to said adjustment rates; and
   a display device that displays a current endoscopic view.

2. The system according to claim 1, wherein said control coordinate system adjusts in correspondence with said current endoscopic view, remaining stationary relative thereto.

3. The system according to claim 1, wherein said control coordinate system is aligned with a natural coordinate system of said endoscope.

4. The system according to claim 1, wherein said control coordinate system is aligned to a user specified orientation.

5. The system according to claim 1, wherein said control coordinate system is aligned with gravity.

6. The system according to claim 1, wherein one or more coordinate systems are displayed on said display device, superimposed on said current endoscopic view.

7. The system according to claim 1, further comprising a depiction of said endoscope.

8. The system according to claim 1, further comprising a depiction of said view vector.

9. The system according to claim 1, further comprising a depiction of one or more coordinate systems.

10. The system according to claim 1, further comprising a depiction of one or more features corresponding to the surroundings of the endoscope.

11. The system according to claim 1, wherein said processing device stores one or more endoscope configurations in a memory thereof.

12. The system according to claim 11, further comprising a display of one or more endoscopic images, each relating to a stored endoscope configuration.

13. A system for viewing the inside of a cavity using a variable direction of view endoscope, wherein a view vector is located at a distal end of said endoscope, comprising:
   an input device that receives commands from a user;
   a tracking device that provides view vector orientation information;
   a processing device that receives said commands and said orientation information and performs operations comprising the calculation of a desired endoscope adjustment rates based on said commands and said orientation information, wherein said commands are interpreted by said processing device with respect to a control coordinate system that can change in alignment with said endoscope, and wherein said endoscope adjusts at said adjustment rates; and
   a viewing device that provides a current endoscopic view.

14. A system for viewing the inside of a cavity using a variable direction of view endoscope, wherein a view vector is located at a distal end of said endoscope, comprising:
   an input means for receiving commands from a user;
   a tracking means for providing view vector orientation information;
   a processing means for receiving said commands and said orientation information and for performing operations, comprising the calculation of desired endoscope adjustment rates based on said commands and said orientation information, wherein said commands are interpreted by said processing device with respect to a control coordinate system that can change in alignment with said endoscope;
   an adjusting means for adjusting said endoscope according to said adjustment rates; and
   a viewing means for providing a current endoscopic view.

* * * * *